US006866776B2

(12) United States Patent
Leason et al.

(10) Patent No.: US 6,866,776 B2
(45) Date of Patent: Mar. 15, 2005

(54) HEATER FOR MASSAGE NODES AND MASSAGE THERAPY DEVICE INCLUDING SAME

(76) Inventors: Wendy Zeller Leason, 28 Garey Dr., Chappaqua, NY (US) 10514; David Leason, 28 Garey Dr., Chappaqua, NY (US) 10514

( * ) Notice: Subject to any disclaimer, the term of this patent is extended or adjusted under 35 U.S.C. 154(b) by 42 days.

(21) Appl. No.: 10/249,090

(22) Filed: Mar. 14, 2003

(65) Prior Publication Data

US 2003/0125648 A1 Jul. 3, 2003

(51) Int. Cl.[7] ............................. H05B 1/00; A61H 15/00
(52) U.S. Cl. ............................ 210/201; 607/96; 601/15; 601/19; 601/113
(58) Field of Search ............................... 219/201, 242, 219/246, 227–229, 429, 432, 433–434; 607/96; 601/15, 19, 112, 113

(56) References Cited

U.S. PATENT DOCUMENTS

| | | | | |
|---|---|---|---|---|
| 2,793,278 A | * | 5/1957 | Anderson et al. | 219/385 |
| 3,489,138 A | * | 1/1970 | Lifschitz | 601/18 |
| 4,103,145 A | * | 7/1978 | Oliveri | 219/222 |
| 4,722,326 A | * | 2/1988 | Ruderian | 601/16 |
| 4,812,616 A | * | 3/1989 | Hong | 219/222 |
| 5,094,225 A | * | 3/1992 | Craw | 601/19 |
| 5,725,484 A | * | 3/1998 | Burnham | 601/128 |
| 5,794,799 A | * | 8/1998 | Collins et al. | 211/70.6 |
| 6,084,211 A | * | 7/2000 | Bauer | 219/242 |
| 6,102,875 A | | 8/2000 | Jones | |
| 6,461,377 B1 | * | 10/2002 | An | 607/96 |
| 2002/0072693 A1 | | 6/2002 | Dehli | |

OTHER PUBLICATIONS

U.S. Appl. No. 60/440,058, filed Jan. 14, 2003, entitled "Apparatus for Combined Application of Massage, Acupressure, and Biomagnetic Therapy".

* cited by examiner

Primary Examiner—Robin O. Evans
Assistant Examiner—Vinod Patel
(74) Attorney, Agent, or Firm—Darby & Darby

(57) ABSTRACT

A base for warming massage nodes of a hand-held therapeutic device includes a housing, terminals connectable to a power supply, a seat for seating the massage nodes, and a heating circuit positioned to provide heat proximate to the massage nodes when the massage nodes are seated in the seat. The massage nodes can comprise an outer layer of stainless steel or iron and a core of material other than or in addition to air. The core absorbs or retains heat for a preferably gradual release over time. A method for warming such massage nodes includes selectively disposing the massage nodes in the housing adjacent to a heater, energizing the heater, permitting the heater to warm the massage nodes, and separating the massage nodes from the heater. The massage nodes can be separated from the heater by a magnetic extraction using the hand-held therapeutic device.

30 Claims, 8 Drawing Sheets

HEATER FOR MASSAGE NODES AND MASSAGE THERAPY DEVICE INCLUDING SAME

BACKGROUND OF INVENTION

The present invention relates generally to handheld massage devices, and more particularly to heating systems for warming nodes of the type used for massage, acupressure, biomagnetic therapy, or a combination of these therapies.

Massage therapy can be provided by a number of known devices. One such device is described in U.S. Pat. No. 6,102,875 to Jones. The Jones device massages via acupressure combined with a biomagnetic therapy. While the apparatus disclosed in the "875 patent may be satisfactory for its intended use, improvements can be had by providing additional modes of therapy during the massage. More particularly one additional mode of therapy is heat. Heat can be applied prior to using a massage device, for example, by taking a warm bath or shower or using a conventional heating pad. Alternatively, a cream can be used to generate an exothermic chemical reaction that can generate heat that is available at the tissue during use of the massage device. The massage device of U.S. Patent Publication No. 2002-0072693 A1 supplies warm air to tissue during the course of massage therapy, the warm air passing through and around vibrating or reciprocating massage nodes.

Heat can be a desirable addition to massage therapy; however, an air stream as in the above-referenced patent publication may be objectionable to some users. Moreover, for some massage devices it can be difficult to deliver heated air to the treatment area. For example, the Jones patent utilizes solid steel or iron balls as the massage nodes that are suspended from a rotating platform and so there is no channel for heated air to flow through the nodes, and because the nodes are continuously revolving on a support it is difficult to deliver a heated air stream proximate to the massage balls.

A problem attendant with the generation of heat is that a great deal of power is consumed. Devices that generate heat typically include power cords to an electrical outlet, yet it would be desirable to have a cordless, hand-held massage device that also provides heat to the treatment area. Heat is also desirable when using metal massage balls (as in Jones) so that they are not cold when initially brought Into contact with skin.

The present invention addresses these and other needs.

SUMMARY OF INVENTION

The present invention pertains to improvements in massage, acupressure and biomagnetic therapies.

In one aspect, the invention provides a base station for use in warming a plurality of massage nodes of a hand-held therapeutic device. The base station includes a housing, terminals that are connectable to a power supply, a seat suitable for seating the massage nodes, and a heating circuit positioned to provide heat proximate to the massage nodes when the massage nodes are seated in the seat.

In more particular aspects, the seat can be shaped to receive at least a portion of the massage nodes in abutting contact, and can have apertures to permit heat from the heating circuit to pass therethrough. The seat can be part of a warming plate that can be removably supported in the housing. Also, spare massage nodes can be stored in the base for heating, as desired.

The massage nodes preferably comprise an outer layer of stainless steel or iron and a core of material other than or in addition to air. The core absorbs or retains heat for a preferably gradual release over time. Such massage nodes can be supplied with the base station. Optionally, movable elements can be provided within the massage nodes and permitted to strike a sound plate to provide a musical effect. The movable elements can include a core material to absorb and radiate heat, or they can move adjacent to such a core.

In another aspect, the invention provides a hand-held therapeutic device with an integral heater for heating the massage nodes. The device in accordance with this aspect of the invention comprises a motor, a rotor driven by the motor and fitted with a plurality of holders, a massage node removably disposed within each of the holders, leads electrically connected to the motor and selectively connectable to a power supply, a magnet positioned between the motor and the rotor and disposed so as to magnetically retain each massage node within a respective holder while permitting rotation of the massage nodes therein, and a heating circuit electrically connected to the leads and configured to heat a thermal mass of the massage nodes.

In a further aspect, the invention provides a method for warming a plurality of massage nodes of the type associated with a hand-held therapeutic device that does not include an integral heater. The method comprises the steps of selectively disposing the massage nodes in a housing adjacent to a heater, energizing the heater, permitting the heater to warm the massage nodes, separating the massage nodes from the heater. As a result, the massage nodes are warmed for use with the hand-held therapeutic device.

In further aspects, the foregoing method can conduct the step of separating the massage nodes from the heater by a magnetic extraction of the massage nodes due to a simple positioning of the hand-held therapeutic device above the housing within a prescribed distance therefrom.

Further aspects and features of the invention can be appreciated from the appended Figures and accompanying written description of certain illustrative embodiments.

BRIEF DESCRIPTION OF DRAWINGS

The invention will be more fully understood by reference to the following drawings, which are for illustrative purposes only.

DETAILED DESCRIPTION

By way of overview and introduction, the present invention imparts heat to massage nodes so that heat can be directly applied to a treatment area during acupressure and biomagnetic therapy or so that the massage nodes are not cold when first applied to skin. In a preferred embodiment, the massage nodes are preheated in a base station so that a hand-held massage device 10 need not include additional circuitry (or impose further weight or drain further power) to obtain the benefit of the present invention. In alternate embodiments, the massage device includes circuitry arranged so as to heat the massage nodes.

Figure 1:
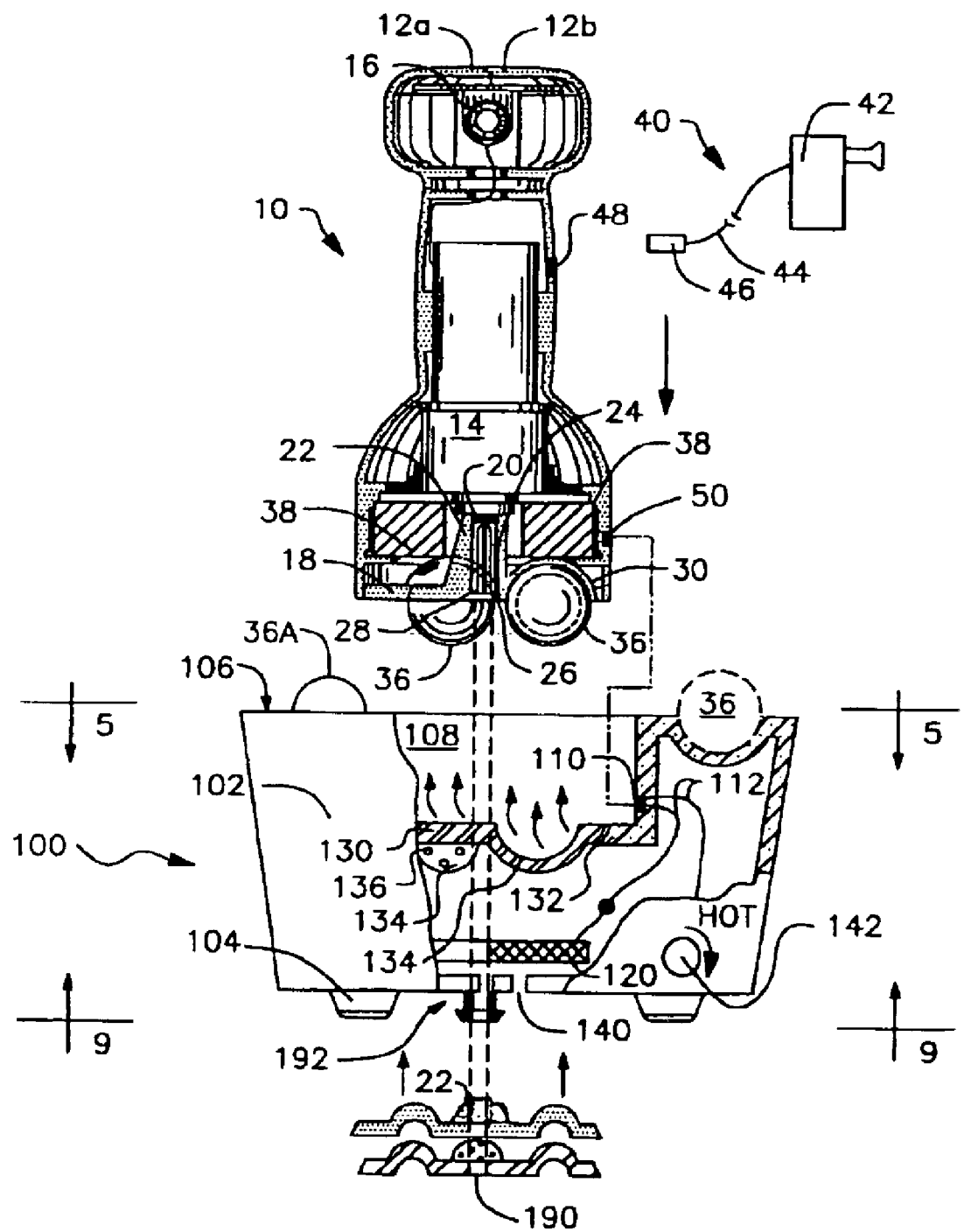
FIG. 1 illustrates a base station, partially in section, operative to heat massage nodes of a handheld massage device. Also illustrated is a sectional view of the massage device of U.S. Provisional Patent Application Ser. No. 60/440,058, filed on Jan. 14, 2003, entitled "Apparatus for Combined Application of Massage, Acupressure, and Biomagnetic Therapy," taken along line 1—1 of FIG. 2.

FIG. 1 illustrates a base station 100 in accordance with a preferred embodiment of the invention. The base station 100 includes a heating circuit, power terminals connectable to a supply of power, and a seat that supports the massage device 10 with the massage nodes in close proximity to a heating element in the heating circuit. The components of the massage device 10 and the base station are described in the sections below.

Illustrative Massage Devices. The preferred embodiment is described in connection with a massage device having stainless steel balls as the massage nodes. The invention has utility with massage devices of different construction and the following description is to be understood as simply presenting an example of a device with which the base station can be used.

The device 10 of FIG. 1 is a handheld massage apparatus that includes, as principal components: a housing 12 (including housing halves 12a and 12b); a motor 14; a power/motor speed control 16; a rotor 18 coupled to a drive shaft 20 of the motor; a plurality of massage nodes 36 comprising stainless steel balls which are freely seated on one side of the rotor: and a magnet 38 disposed on a second side of the rotor.

Figure 1B:
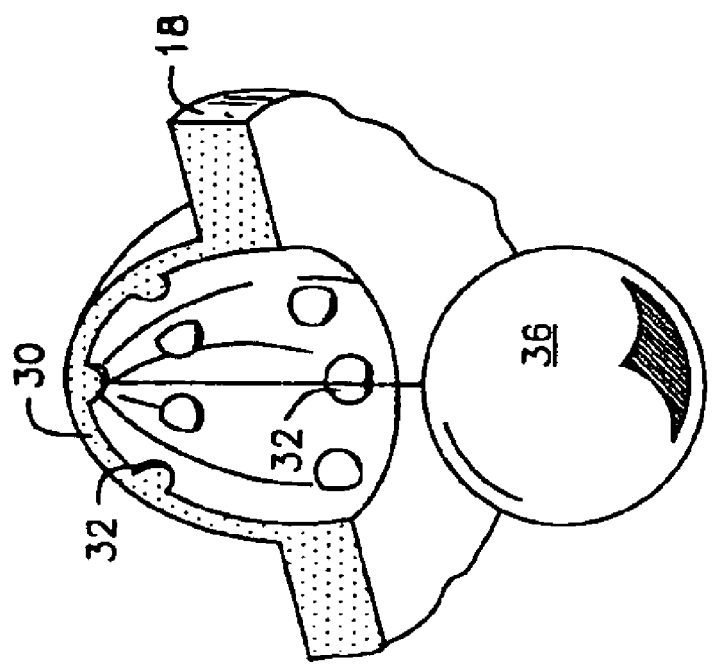
FIG. 1B is an exploded perspective view in partial cross-section of a section of the rotor of FIG. 1, with the massage node (shown embodied as a ball) being displaced therefrom.
Figure 1A:
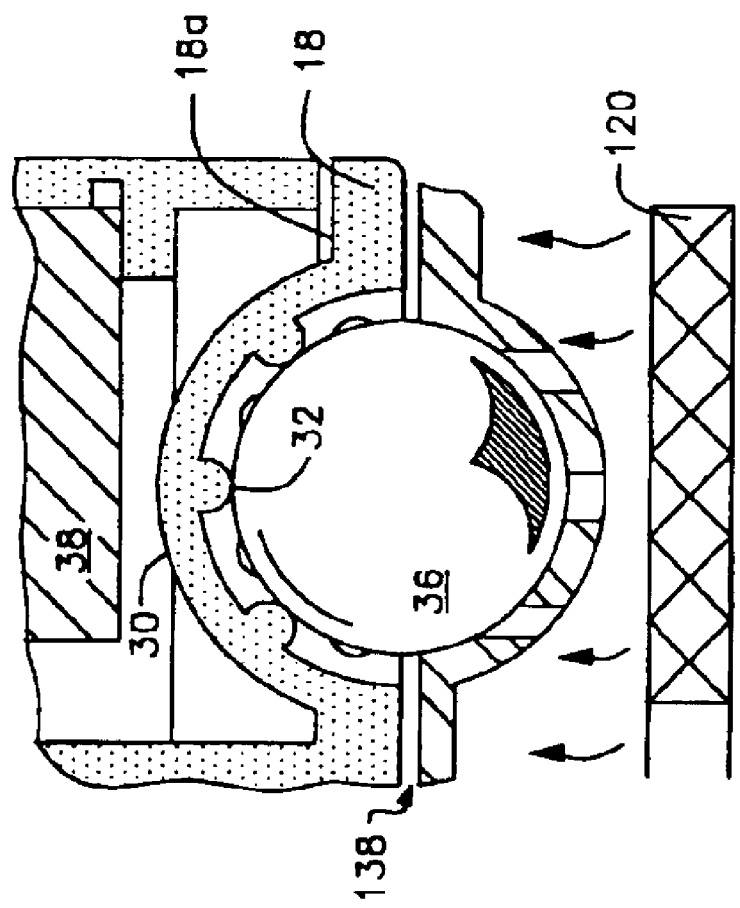
FIG. 1A is a partial cross-sectional view of the rotor of FIG. 1.

The rotor includes a seat 30 for each of the massage nodes, and each seat in the illustrated embodiment has a depth that approximates the radius of the massage nodes. The depth of the seat is established so as to prevent the massage nodes from being dislodged during normal usage conditions of the device 10, which can include, for example, a variable rotational speed of the rotor 18 (of between approximately 25 and approximately 75 rpm) coupled with downward and lateral pressure exerted by the user against a person's body. As shown in the detail of FIG. 1A, the seats preferably comprise generally hemispherically shaped domes that are formed at and behind an inner face of the rotor 18 (that is, on a side 18A of the rotor closer to the magnet 38). This arrangement better enables the components within the housing 12 to remain free of debris, dirt, and massage oils. Because the rotor 18 is preferably formed of a plastic material, positioning a solid, dome-like seat 30 between each node 36 and the magnet 38 does not adversely impact the magnetic field strength experienced by the node. On the other hand, the dome seat traps heat provided by the base station and assists in warming the massage nodes when the device 10 is seated in the base station, as described below.

It will be appreciated that surface modifying features can be added to the seats 30 to reduce the friction between the nodes 36 and the seat itself. For example and as shown most clearly in the detail view of FIG. 1B, a plurality of bumps 32, can be formed on the inner surface of the seat to reduce the contact area between the balls 36 and the seat. By reducing the contact area between the nodes 36 and the seat 30, friction between the two is likewise reduced and the balls 36 can rotate with a comparatively lower frictional coefficient.

Figure 2:
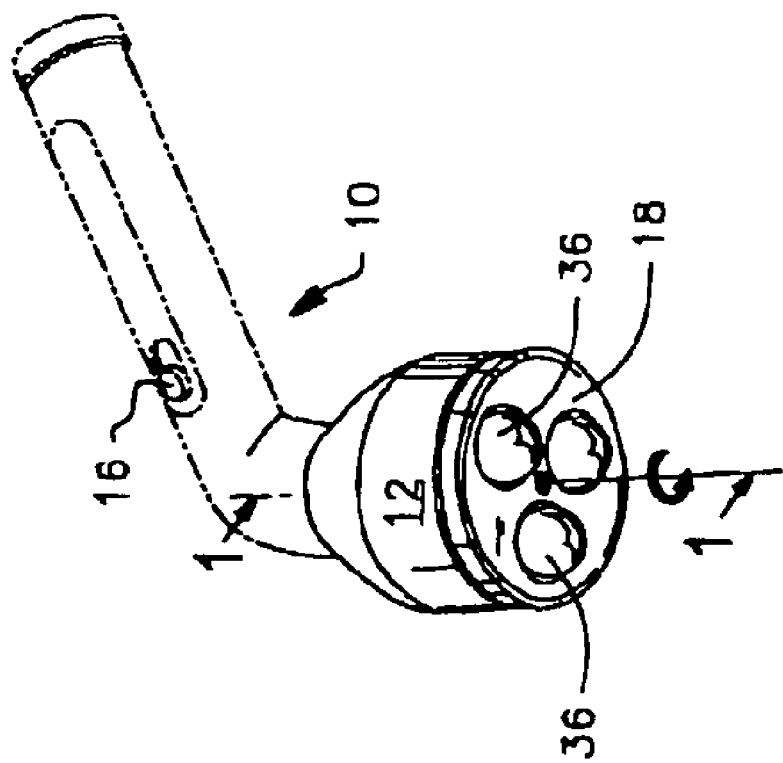
FIG. 2 is a perspective view of the massage device of FIG. 1, now showing in phantom line a handle oriented off-axis of the operative massage surface.

As shown in FIG. 2, the device 10 has three seats 30 and a corresponding number of massage nodes arranged in a triangular fashion. When the motor is energized, the rotor rotates and the massage nodes 36 are journaled about the shaft 20, thereby providing a "kneading" motion to the user when the nodes are pressed against skin. It will be appreciated that the kneading motion can also be produced with fewer or a greater number of nodes. Thus, for example, a rotor 58 as shown in FIG. 3 has four seats 30 for receiving massage nodes 36A, which are smaller than massage nodes 36.

Figure 3:
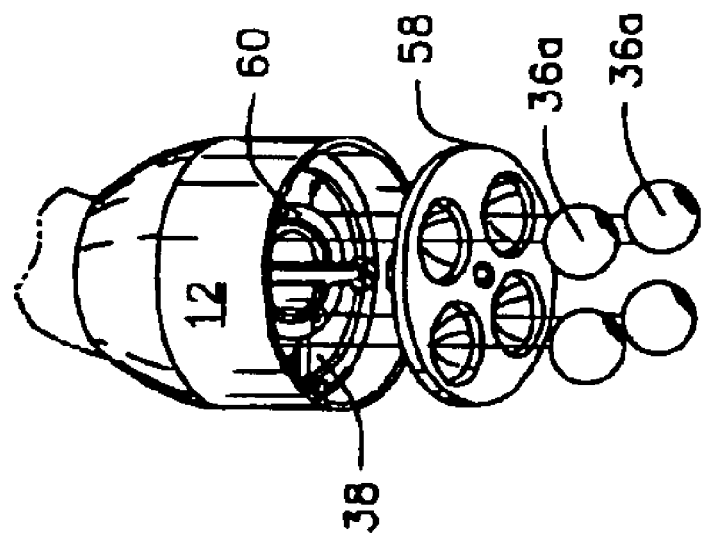
FIG. 3 is an exploded view of the massage head of FIG. 1, fitted with a rotor that is configured to seat four massage nodes.

FIG. 3 further shows an optional heater 60 integrated into the mechanism of the massage device. The heater 60 is positioned to impart heat to the massage nodes. The heater is part of a heating circuit, as described below. If the heater is so positioned, heat can be continuously supplied during massage therapy to the massage nodes. This has benefits in a corded device; however, in a cordless device, the continued supply of heat will shorten the useful charge on the batteries and so use of the base station 100 is preferred when the massage nodes of a cordless device are to be heated.

The magnet 38 is a preferred component for holding the massage nodes 36 within their respective seats 30. The magnet is preferably an annular magnet and is preferably arranged to underlie the rotational path of the massage nodes, but can instead comprise a plurality of magnets placed along that same path. The magnet 38 can be on the order of 1000 Gauss in strength, for example, or an electromagnet supplied with current from a power supply and a transistor- or rheostat-based control circuit can be used to provide a variable Gauss output.

By providing massage nodes 36 in the form of balls of steel, iron or the like, they can be held in place by the magnet 38 and can universally and freely rotate as the rotor 18 rotates. Such materials for the massage nodes permit magnetic fields to transfer from the magnet 38 through the nodes 36 and into any tissue contacting the balls 36. The massage nodes have a mass that is heated (a "thermal mass") but more preferably are constructed so as to include an outer layer, say, of stainless steel, and a core of a heat-absorbent material having additional thermal mass suitable for retaining heat absorbed from the heating circuit (described below) and for slowly radiating such heat while the device 10 is in use treating muscles and other tissue. Thus, instead of a solid metal or an air-core surrounded by an outer layer of stainless steel or iron, the massage nodes 36 preferably are constructed so as to have an augmented thermal mass, which is engineered to absorb and release heat better than a solid or hollow steel or iron node, disposed within the outer layer.

The massage nodes optionally can include internal, movable elements that are free to strike a sound plate as the nodes are revolved by the rotor or in response to contact with skin. As the movable element strikes the sound plate, a musical affect results. For example, the massage nodes can be arranged to provide varying pitches from low to high for a soothing effect. Preferably, the movable elements include a core material as previously described s as to absorb and radiate heat, or the movable elements are arranged to move adjacent to such a core within the massage nodes 36, 36A. Iron balls that include a sound plate are available from Baoding Iron Hollow Ball Plant, Baoding City, Hebei Province, China.

Preferably, the rotor 18 includes a central collar 22 that couples to the shaft 20 by means of an intermediate sleeve 24 that is pressed onto the shaft 20. Conveniently, the shaft 20 and collar 22 can pass through the center of the annular magnet 38 if an annular magnet is used. The sleeve 24 preferably has a flared circumferential end 26 that engages an annular detent 28 in the collar 22. In this way, the rotor 18 can be removed from shaft 20 by separating the collar 22 from the sleeve 24 with a longitudinal pulling motion (see FIG. 3). Once removed, the rotor 18 can be cleaned, sterilized, replaced or swapped for a different rotor. The collar 22 can be coupled to the shaft 20 in other ways, such as by a set screw (not shown) or other conventional coupling means.

Figure 4:
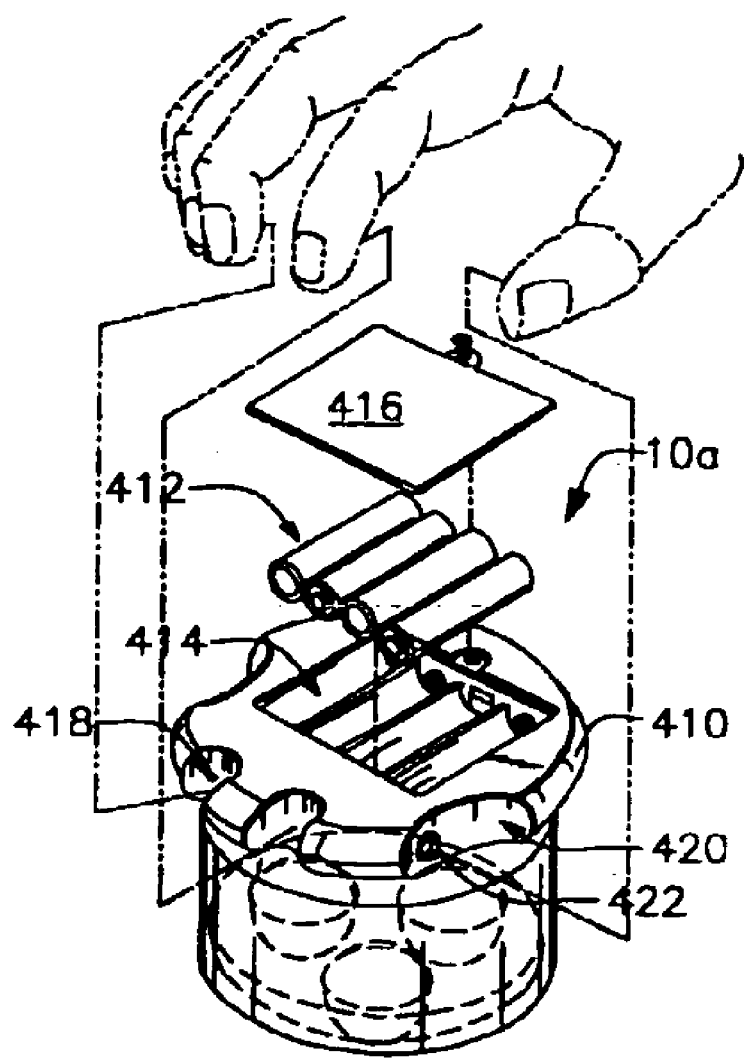
FIG. 4 is a perspective view, partially exploded, of a handheld accupressure and biomagnetic therapy device in accordance with another embodiment.

FIG. 4 illustrates a second embodiment comprising a palm-held massage device 10A. In addition to the principal components discussed above in connection with FIG. 1, the embodiment of FIG. 1A illustrates a number of batteries 412, optionally rechargeable batteries, disposed within a battery compartment 414, under a cover 416. (Of course, the device 10 of FIG. 1 can utilize internal batteries as well to energize the motor 14, or can utilize an external power supply 40—comprising a transformer 42, power cord 44 and plug 46—which couples to the motor 14 via a jack 48.) The device 10A includes features that permit the user to easily grasp the housing with one or more fingers. For example, there are finger slots 418, a thumb slot 420, and a control button 422 proximate to the thumb slot to permit easy thumb activation of the device 10A.

The handheld device 10 allows a therapist or even the patient to apply gentle massaging pressure directly to a muscle. The magnet holding the balls in place allows the balls to freely rotate over the muscle in a circular motion while the balls are driven along a circular path by the rotor. This action creates a kneading effect over the soft tissues of the muscle minimizing the resistance created by rolling over the muscle. The rotating motion of the device combined with application of magnetic force can help to eliminate toxins and waste products to permit the treatment area to be replenished with oxygen-rich blood and nutrients. The addition of heat can further catalyze these desired effects. The muscle's natural healing process can thereby be enhanced, which may further bolster the area's resistance to degenerative effects. Consequently, such a device can ease pain, increase circulation, and invigorate muscles to better speed recovery.

For a more detailed description of the massage device 10, see U.S. Provisional Patent Application Ser. No. 60/440,058, filed on Jan. 14, 2003, entitled "Apparatus for Combined Application of Massage, Acupressure, and Biomagnetic Therapy," the entirety of which is hereby incorporated by reference. In addition, U.S. Pat. No. 6,102,875 of Jones is hereby incorporated by reference as if set forth in its entirety herein.

Base Station. Referring again to FIGS. 1 and 1A, the base station 100 includes a housing 102 supported by feet 104. An upper surface 106 of the housing is configured to receive the massage device 10 into a mouth 108 and, optionally, can be configured to store spare massage nodes 36, 36A. Preferably, the mouth 108 is sized and shaped to snugly fit the massage device 10. The mouth 108 can be fitted with terminals 110 that engage contacts 50 disposed on the massage device 10 while the massage device is seated in the housing 102. The terminals 110 can receive power from the massage device 10 that is sourced by the transformer 42 through the jack 48. Alternatively, the terminals 110 can be located elsewhere, can receive power from another source (e.g., via a direct connection to a power supply), or both. Wires 112 extend from the power terminals 110 to a heating circuit 150, described below.

Figure 5:
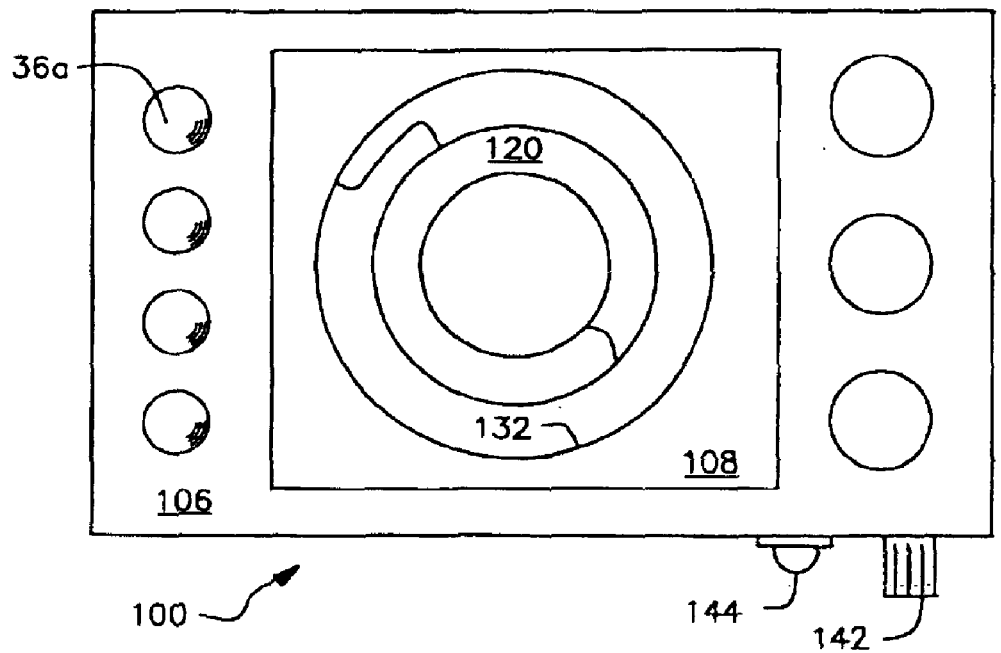
FIG. 5 is a top plan view of the base station of FIG. 1 taken along lines 5—5.

As can be seen in FIGS. 1, 1A and 5, a heater 120 is disposed within the mouth. Heat produced by the heater rises upward toward the upper surface 106. A warming plate 130 preferably made out of stainless steel or other heat-conductive material, rests above the heater 120, preferably upon a ledge 132, and defines a seat that supports the massage device when placed in the base station. The warming plate preferably includes a plurality of recesses 134 which preferably have a degree of curvature that is complimentary to the degree of curvature of the massage nodes 36 or 36A so that the nodes can at least partially yet snugly seat within the recesses. The recesses thus have a concavity sized to receive at least a portion of a respective massage node. Of course, recesses need not be provided in the warming plate, but it is preferred that there be intimate contact between the nodes 36 and portions of the warming plate for efficient and rapid heat transfer therebetween.

Convection currents naturally rise from the heater 120 upward to the warming plate 130. Apertures 136 in the recesses 134 and optionally elsewhere through the warming plate permit heated air to pass beyond the warming plate into a gap 138 between the top of the warming plate and the exterior face of the rotor 18. Some of the heated air passes upward into the seat 30 behind the massage nodes 36, 36A (between the bumps 32) and that improves the transfer of heat from the heater 120 to the massage nodes. Vent holes 140 are preferably provided below the heater 120 to passively draw in unheated air while heated air rises within and out of the housing 102.

A control knob 142 permits a user to turn the heater on or off. Preferably, the control knob is coupled to a rheostat or transistor circuit that further permits the user to select a heating temperature, say, between warm and hot. The setting of the rheostat governs how much current flows through the heating element and, consequently, how much heat is generated in a given period of time. Optionally, a temperature regulator circuit can be utilized to more closely govern the operating temperature of the heater. An indicator 144 such as a light emitting diode ("LED") preferably is included in the heating circuit to indicate whether the heater is on or off.

Figure 6:
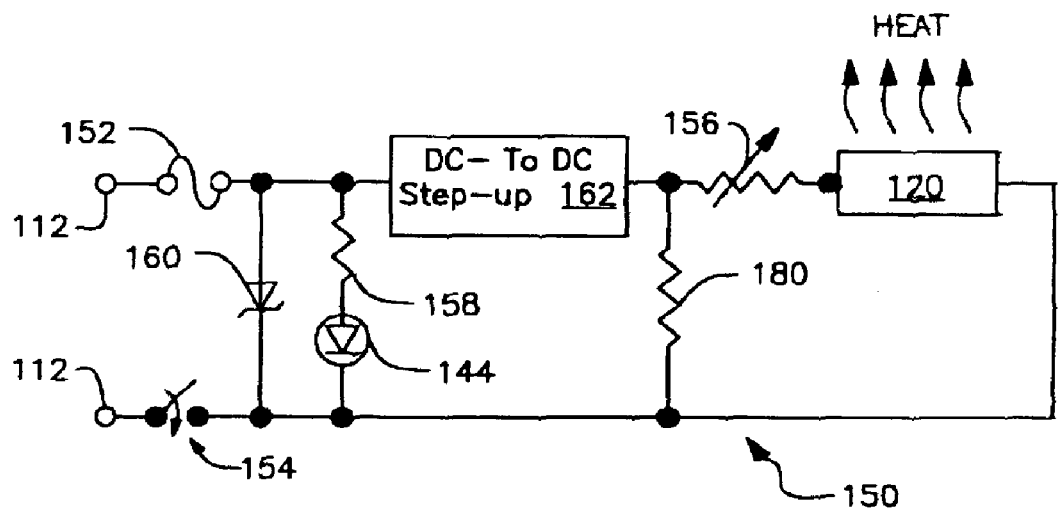
FIG. 6 is a schematic diagram of a heating circuit operable with the base station of FIG. 1.

Referring now to FIG. 6, the heating circuit 150 is supplied with power via wires 112. The power on supply lines may be, for example, twelve volts D.C. A fuse 152 protects the heating circuit from overload conditions, in a conventional manner. A switch 154 governs the on/off state of the circuit, and in the preferred embodiment is coupled with a variable resistor 156 which is used to vary the current flowing to the heating element and, consequently, the amount of heat provided by the circuit. The indicator 144 receives a driving voltage from the supply lines when the switch 154 is closed. Typically, a resistor 158 is provided in series with the indicator to drop the driving voltage to a suitable level, and a zener diode 160 is in parallel with the indicator to prevent voltage overload. The switch 154 can be positioned within the mouth 108 so as to change states (on to off and off to on) with insertion and removal of the massage device 10.

A step-up transformer 162 receives power from the supply lines 112 and steps it up to a higher D.C. value. This higher voltage is then dropped across a voltage divider circuit comprising the rheostat 156 and a heating element 120, preferably in the form of a ceramic resistor of low ohmic value, on the one hand, and a high impedance element 180 on the other. The ceramic resistor is the load in a circuit path that receives substantially all of the current. As a result, the ceramic resistor gets hot and the heating element 120 produces heat.

Figure 7:
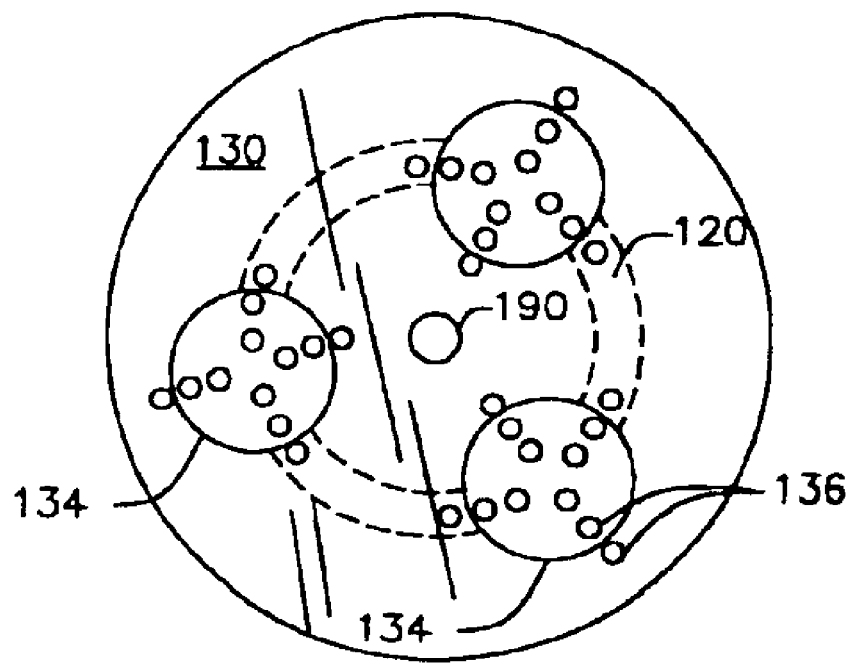
FIG. 7 is a top plan view of one embodiment of the warming plate that is configured to receive three massage nodes.
Figure 8:
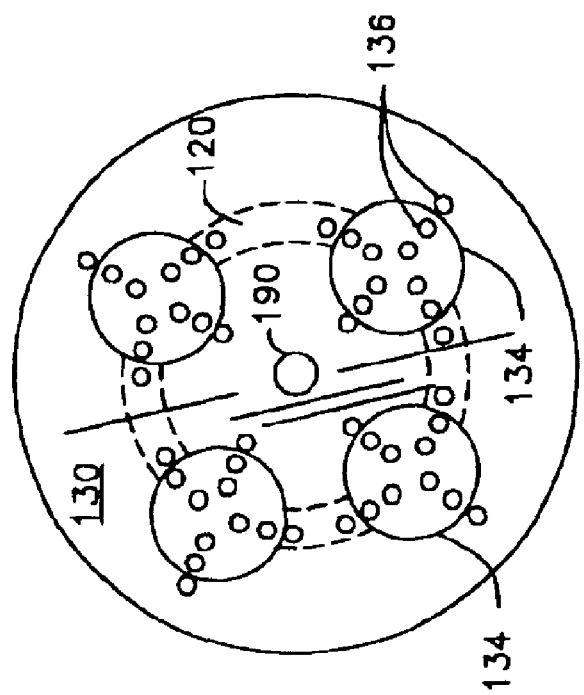
FIG. 8 is a top plan view of another embodiment of the warming plate, now configured to receive four massage nodes.

Referring now to FIGS. 7 and 8, which are a top plan views of two embodiments of the warming plates 130, the heating element 120 preferably has the form of an annular ring that is sized so as to underlie the path traversed by the massage nodes 36, 36A. Thus, the recesses 134 are generally disposed above the heating element, as are a substantial number of the apertures 136. As noted above, the warming plates are preferably made of a heat conductive material such as stainless steel.

Figure 7A:
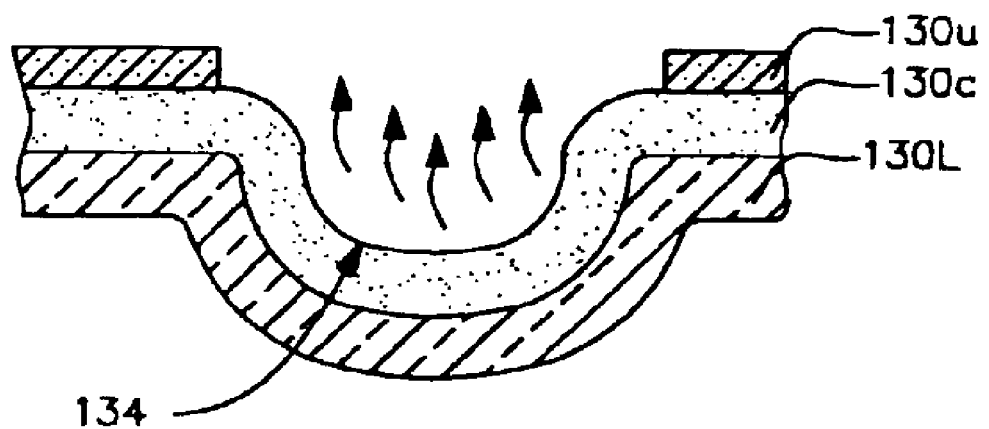
FIG. 7A is a detail, sectional view of a portion of the warming plate of FIG. 7.

Optionally, the warming plates can include an insulative material over its upper and lower surfaces. If an insulative material is provided, it is preferably disposed over the entire surface of the warming plate except for within the recesses 134. As shown in the detailed cross-sectional view of FIG. 7A, the warming plate comprises a central heat-conductive layer 130C which also provides structural rigidity to the warming plate, an upper insulative layer 130U which can be any of a variety of (preferably transparent) polymers, and a lower insulative layer 130L which can be the same as layer 130U. The lower layer 130L is optional, but if provided is preferably continuous and thinner than the upper layer 130L. These layers cooperate to promote heat travel toward the recesses where there is no upper insulation and so heat can be more readily transferred to the massage nodes 36 or dissipated.

FIGS. 7 and 8 illustrate an optional feature in accordance with a preferred embodiment of the invention. Each warming plate 130 can be provided with a central aperture 190 that can be engaged to a mount 192 on an undersurface of the base station 100 for storage. Thus, two warming plates can be accommodated by the base station 100 at one time by placing one warming plate in an operative position within the mouth 108 upon the ledge 132 while the other warming plate is secured to the mount 192.

Figure 9:
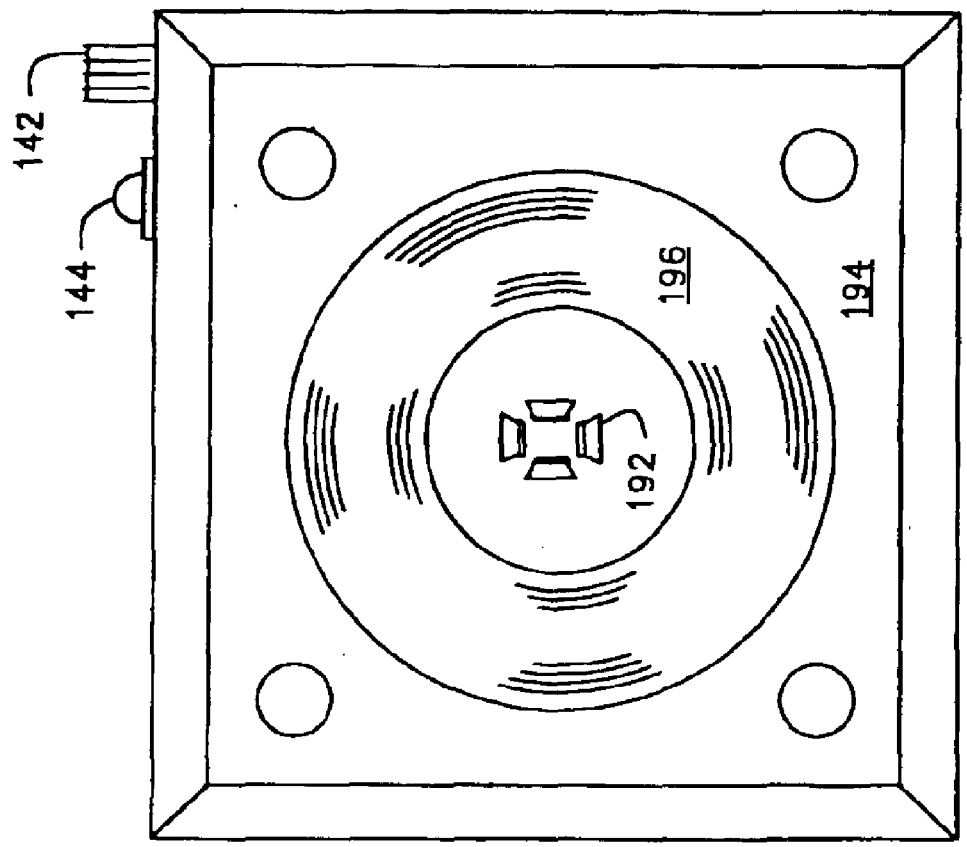
FIG. 9 is a bottom plan view of the base station of FIG. 1 taken along lines 9—9.

With reference now to FIGS. 1 and 9, a lower surface 194 of the base station 100 has the mount 192 projecting therefrom between the feet 104. A groove 196 circumscribes the mount and is sized and shaped to receive either the rotor 18, 58 plus one of the warming plates 130. Thus, a spare rotor can be provided and stored with the base station 100, and a suitably configured warming plate can also be provided and stored with the base station.

Figure 10:
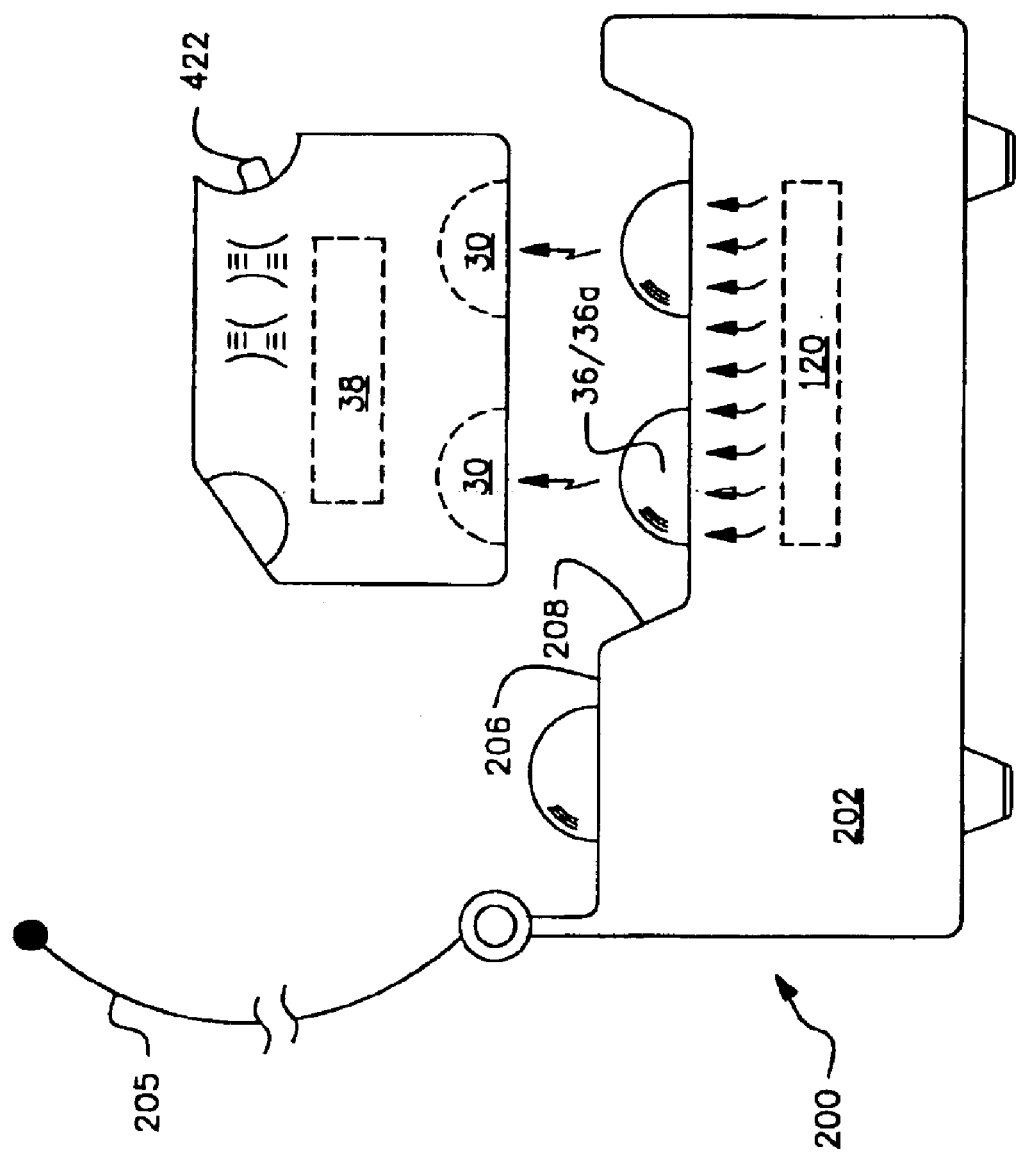
FIG. 10 illustrates a second embodiment of a base station in accordance with the invention, this embodiment having a lid and being configured to receive massage nodes clear of any massage device.

FIG. 10 shows a second embodiment of a base station 200 in which an enlarged mouth 208 permits the massage nodes 36 or 36A to be seated directly on a warming plate, preferably within recesses 134 which are aligned with the seats 30, as previously described. A heating circuit warms the nodes, also as previously described, and the nodes can be manually removed, or, more preferably, can be magnetically withdrawn by placing the massage device 10 above the base station 200, in the vicinity of the massage nodes. In this way, the massage balls are drawn upwardly by a magnetic attraction between the nodes 36 and the magnet 38 and are engaged to the rotor 18, 58 without the user having to touch the heated nodes. Additional nodes can be stored on or remote from the heater (the latter being shown in FIG. 10) and can be heated while the other set is placed into service. A cover 205 is optionally provided and positionable so as to cover the base station 200.

Operation of the Preferred-Embodiment. In use, the massage device 10 can be disposed in the base station 100 to position the massage nodes 36 adjacent to the heater 120. The heater can be automatically energized upon placement of the massage device in the base station 100, or can be manually actuated by the control knob 142 (e.g., when using either base station 100 or 200). The user permits the massage nodes to be warmed by the heater by, say, leaving the nodes adjacent the heater for a period of time. The massage nodes are thereafter separated from the heater for use by the user.

Alternatively, the massage nodes can be disposed adjacent to the heater 120, for example, on a warming plate, independent of any massage device. That is, the massage nodes can be removed from the massage device or a spare set of nodes can be the nodes placed adjacent to the heater. As described above, the heater is energized and the massage balls adjacent to the heater are permitted to warm. The heated massage nodes can be separated from the heater manually, but it is preferred that they be magnetically lifted from the base station by hovering the massage device above the massage nodes at a distance sufficiently close so that a magnetic force of attraction due to the magnet 38 overcomes the weight of the massage nodes 36, 36A and draws them into respective seats 30. Once the massage nodes have separated from the heater 120, a spare set of massage nodes can be disposed adjacent to the heater for warming while the first set is in use.

While this invention has been particularly shown and described with references to certain embodiments thereof, it will be understood by those skilled in the art that various changes in form and details may be made therein without departing from the scope of the invention encompassed by the appended claims.

What is claimed is:

1. A base station for use in warming a plurality of massage nodes of a separate, hand-held therapeutic device, comprising:
   (a) a housing;
   (b) first terminals associated with the housing connectable to a power supply;
   (c) a seat suitable for seating the massage nodes; and
   (d) a heating circuit in the housing and positioned to provide heat proximate to the massage nodes when the massage nodes are seated in the seat;
   wherein the hand-held therapeutic device includes rechargeable batteries and wherein the base station further comprises leads connecting the rechargeable batteries to the power supply when the hand-held therapeutic device is seated in the housing.

2. The base station of claim 1, wherein the seat includes recesses that are shaped with a degree of curvature that is complementary to at least a portion of the massage nodes.

3. The base station of claim 2, wherein the recesses include apertures, the apertures permitting heat from the heating circuit to pass therethrough.

4. The base station of claim 1, wherein the seat includes apertures, the apertures permitting heat from the heating circuit to pass therethrough.

5. The base station of claim 4, wherein the heating circuit includes a heater, the base station further comprising a vent in the housing, the vent being positioned below the heater.

6. The base station of claim 1, wherein the seat comprises a warming plate.

7. The base station of claim 6, wherein the warming plate is made of a heat conductive material.

8. The base station of claim 7, wherein the heat conductive material is stainless steel and wherein the warming plate further comprises at least one insulative layer abutting the conductive material.

9. The base station of claim 6, wherein the warming plate is removably supported in the housing.

10. The base station of claim 6, wherein the warming plate includes apertures, the apertures permitting heat from the heating circuit to pass therethrough.

11. The base station of claim 6, further comprising a clip on the housing and wherein the warming plate has an aperture sized to be mounted on the clip.

12. The base station of claim 11, further comprising feet disposed on the housing and sized to position the housing above a planar supporting surface so that the clip is suspended clear of the planar support.

13. The base station of claim 1, wherein the heating circuit includes a heater and a user-operated control electrically connected so that manual adjustments at the user-operated control effect a change in temperature of the heater.

14. The base station of claim 13, wherein the user-operated control is electrically connected to permit a user to turn off the heating circuit.

15. The base station of claim 1, wherein the heating circuit includes a ceramic resistor defining a heater.

16. The base station of claim 1, wherein the heating circuit includes a DC-to-DC voltage step-up circuit.

17. The base station of claim 1, wherein the seat is suitable for seating the hand-held therapeutic device together with the massage nodes protruding therefrom and wherein the heating circuit provides heat to the massage nodes while the hand-held therapeutic device is seated in the housing.

18. The base station of claim 17, further comprising receptacles positioned remote from the seat and shaped to receive spare massage nodes.

19. The base station of claim 17, further comprising a switch operative to disengage the heating circuit upon removal of the hand-held therapeutic device from the seat.

20. The base station of claim 1, wherein the massage nodes comprise an outer layer of stainless steel and a core of a heat absorbent material.

21. A two-piece massage device, comprising:
a cordless hand-held therapeutic device; and
a base station configured to warm the massage nodes for use in the cordless hand-held therapeutic device,
the cordless hand-held therapeutic device comprising:
a motor;
a rotor driven by the motor and fitted with a plurality of holders;
a massage node removably disposed within each of the holders, each massage node being ferromagnetic;
leads electrically connected to a first power supply and selectively connectable to the motor to selectively drive the rotor;
a magnet positioned between the motor and the rotor and disposed so as to magnetically retain each massage node within a respective holder while permitting rotation of the massage nodes therein; and
the base station comprising:
a first housing;
first terminals associated with the first housing connectable to a second power supply;
a seat suitable for seating the massage nodes; and
a heating circuit in the housing and positioned to provide heat proximate to the massage nodes when the massage nodes of the cordless hand-held therapeutic device are seated in the seat and to provide warmed massage nodes for use in the cordless hand-held therapeutic device when the cordless hand-held therapeutic device is unseated from the base station.

22. The two-piece massage device of claim 21, further comprising:
a rechargeable battery as the first power supply;
a second housing disposed about the cordless hand-held therapeutic device;
first contacts on the second housing connectable to the leads; and
second contacts positioned on the base station so as to electrically connect to the leads of the cordless hand-held therapeutic device when seated in the seat,
wherein the rechargeable battery is chargeable while the cordless hand-held therapeutic device is seated in the first housing of the base station.

23. The two-piece massage device of claim 21, wherein the massage nodes comprise metallic balls.

24. The two-piece massage device of claim 23, wherein the permitted rotation of the metallic balls is universal rotation.

25. The two-piece massage device of claim 21, wherein the massage nodes comprise rollers.

26. The two-piece massage device of claim 21, wherein the seat includes recesses that are shaped with a degree of curvature that is complementary to at least a portion of the massage nodes.

27. The two-piece massage device of claim 21, wherein the seat comprises a warming plate.

28. The two-piece massage device of claim 21, wherein the heating circuit includes a DC-to-DC voltage step-up circuit.

29. The two-piece massage device of claim 21, further comprising receptacles positioned remote from the seat and shaped to receive spare massage nodes.

30. The two-piece massage device of claim 21, further comprising a switch operative to disengage the heating circuit upon removal of the cordless hand-held therapeutic device from the seat.

* * * * *